United States Patent [19]

Srivastava et al.

[11] Patent Number: 5,380,931
[45] Date of Patent: Jan. 10, 1995

[54] OXIDATIVE CLEAVAGE OF POLYETHYLENICALLY UNSATURATED COMPOUND TO PRODUCE CARBOXYLIC ACID

[75] Inventors: Devendra K. Srivastava, Fargo, N. Dak.; Mashupye M. Kgaphola, Marishane, South Africa

[73] Assignee: NDSU Research Foundation, Fargo, N. Dak.

[21] Appl. No.: 144,974

[22] Filed: Oct. 27, 1993

[51] Int. Cl.$^6$ .............................................. C07C 51/16
[52] U.S. Cl. .................................... 562/542; 562/543; 562/544
[58] Field of Search ........................ 562/542, 543, 544; 522/44, 79, 83, 103; 502/165, 168

[56] References Cited

U.S. PATENT DOCUMENTS

| | | |
|---|---|---|
| 2,133,008 | 10/1938 | Ralston et al. . |
| 2,203,628 | 6/1940 | Hopff et al. . |
| 2,203,680 | 5/1940 | Ellingboe . |
| 2,226,357 | 12/1940 | Olin et al. . |
| 2,676,186 | 4/1954 | Dunlop et al. . |
| 3,031,482 | 4/1962 | Stein et al. . |
| 3,890,246 | 6/1975 | Grasselli et al. . |
| 4,052,418 | 10/1977 | Suresh et al. . |
| 4,098,817 | 7/1978 | Barone .............................. 562/543 X |
| 4,099,018 | 7/1978 | Stapp . |
| 4,293,443 | 10/1981 | Suresh et al. . |
| 4,309,310 | 1/1982 | Callahan .............................. 502/165 |
| 4,331,608 | 5/1982 | Kawamoto et al. . |
| 4,532,079 | 7/1985 | Venturello et al. ................ 562/543 |
| 4,606,863 | 8/1986 | Nakazawa et al. . |
| 4,833,272 | 5/1989 | Nakazawa et al. . |
| 4,868,328 | 9/1989 | Drent . |
| 4,931,590 | 6/1990 | Kummer et al. . |
| 5,041,470 | 8/1991 | Gelorme et al. ..................... 522/44 |

FOREIGN PATENT DOCUMENTS

| | | |
|---|---|---|
| 599242 | 6/1960 | Canada . |
| 524163 | 7/1940 | United Kingdom . |
| 652355 | 4/1951 | United Kingdom . |
| 1442748 | 7/1976 | United Kingdom . |

OTHER PUBLICATIONS

Hudlicky, "Oxidations", *Oxidations in Organic Chemistry*, American Chemical Society, 77–90 (1990).

Ishii et al., "Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2-Diols, and Olefins", *J. Org. Chem.*, 53, 3587–3593 (1988).

Oguchi et al., "Oxidative Cleavage of Olefins into Carboxylic Acids with Hydrogen Peroxide by Tungstic Acid", *Chemistry Letters*, The Chemical of Society of Japan, 857–860 (1989).

Sheldon et al., "Metal Catalysts in Peroxide Reactions", *Metal-Catalyzed Oxidations of Organic Compounds*, Academic Press, 49–56 (1981).

Zaldman et al., "Double Bond Oxidation of Unsaturated Fatty Acids", *JAOCS*, 65, 611–615 (1988).

*Primary Examiner*—Arthur C. Prescott

[57] ABSTRACT

A method of oxidatively cleaving polyethylenically unsaturated compound having a pair of carbon atoms ethylenically bonded to other carbon atoms but singly bonded to each other or a pair of carbon atoms ethylenically bonded to other carbon atoms but separated from each other by a saturated carbon atom to produce a carboxylic acid is disclosed. A hydroperoxide such as hydrogen peroxide is used as the oxidant and a salt of vanadic acid such as sodium metavanadate is used as a catalyst to oxidatively cleave such an unsaturated compound in a polar organic solvent. Ethylenically unsaturated compounds that do not contain carbon-carbon double bonds separated by one or two carbon-carbon single bonds, such as a monoethylenically unsaturated carboxylic acid present in a mixture with the polyethylenically unsaturated compound, are not oxidized or only minimally oxidized.

22 Claims, No Drawings

OXIDATIVE CLEAVAGE OF POLYETHYLENICALLY UNSATURATED COMPOUND TO PRODUCE CARBOXYLIC ACID

FIELD OF THE INVENTION

This invention relates to a method for catalytic oxidative cleavage of polyethylenically unsaturated compounds with an oxidant in a solvent to produce carboxylic acids.

BACKGROUND OF THE INVENTION

Carboxylic acids are commercially important. They can be used as ingredients for making plasticizers, lubricants, dielectric fluids, and synthetic fibers. The short-chain aliphatic carboxylic acids are colorless liquids, each of which has a characteristic odor that is often sharp or penetrating. For example, the distinctive taste and odor of acetic acid make it an important flavoring agent.

Fatty acids are long chain (generally about $C_4$ or greater) carboxylic acids. Naturally occurring fatty acids generally have 10 to 22 carbons. Some fatty acids have commercial uses. For example, oleic acid can be used for making plasticizers, coatings, etc. The higher fatty acids are generally derived from animal oils, vegetable oils, and fish oils. Often, when an oil is hydrolyzed, a mixture of fatty acids is formed. Such mixtures usually contain both monoethylenically unsaturated and polyethylenically unsaturated fatty acids. Generally unsaturated carboxylic acids can be oxidatively cleaved to form smaller molecular weight carboxylic acids.

A number of methods have been disclosed to oxidatively cleave the double bonds of unsaturated compounds to form carboxylic acids. In these reactions, oxidants and catalysts are generally required. Olin et al. (U.S. Pat. No. 2,226,357) disclose a method for producing polycarboxylic acids by treating cyclo-aliphatic olefins with sulfuric acid and subsequently treating the sulfation product with nitric acid or other oxidants in the presence of a catalyst such as vanadic acid.

Ellingboe (GB Patent No. 524,163) and U.S. Pat. No. 2,203,680), discloses a method for producing saturated aliphatic carboxylic acids by the oxidation of long chain unsaturated fatty acids, such as oleic acid, erucic acid, linoleic acid, and linolenic acid, with highly concentrated nitric acid. The oxidation reaction is catalyzed by a catalyst, namely a vanadium compound such as ammonium vanadate.

Although the above methods can be used for producing carboxylic acids, the use of nitric acids is problematic. Often, toxic gases ($NO_x$), as well as other undesirable oxidation side-products are produced. The $NO_x$ gases present a health problem. Further, processing necessary to remove the undesirable side products results in increased cost of production for the desired products.

Other oxidants have also been used for the oxidative production of carboxylic acids. Ralston et al. (U.S. Pat. No. 2,133,008) disclose a process for cleaving unsaturated fatty acids, glycerides thereof, and water soluble soaps thereof by an alkali metal hypochlorite in the presence of a hypochlorite-decomposing agent. The suitable hypochlorite-decomposing agents disclosed include iron, cobalt, manganese, and nickel compounds. Dunlop et al. (U.S. Pat. No. 2,676,186) disclose the oxidation of levulinic acid to succinic acid. In this reaction, vanadium pentoxide is used as a catalyst, and air or other oxygen-containing gas is used as an oxidant. Zaidman et al., *J. AM. Oil Chem. Soc.*, 65:611-615 (1988) disclose the use of oxidants, such as ozone, sodium hypochlorite, potassium permanganate, potassium bichromate, chromic acid, and hydrogen peroxide, for the oxidation of unsaturated fatty acids.

Several methods based on the use of hydrogen peroxide as the oxidant for producing carboxylic acids are known. For example, Nakazawa (U.S. Pat. No. 4,833,272) discloses the use of hydrogen peroxide in oxidizing a Dieis-Alder reaction product of maleic anhydride and a diene and/or the corresponding acid catalyzed by at least one of tungstic acid, molybdic acid, heteropoly acids thereof, and mixed coordination heteropoly acids. Nakazawa et al. (U.S. Pat. No. 4,606,863) disclose a process for preparing carboxylic acid by subjecting an oxidation product produced by reacting a peroxide with an unsaturated aliphatic monocarboxylic acid or aliphatic olefin to oxidation by oxygen or oxygen-containing gas in the presence of a catalyst. Other than hydrogen peroxide, a few other hydroperoxides are also disclosed.

A variety of catalysts has been used to catalyze oxidative reaction to produce carboxylic acids. Ellingboe (GB Patent No. 524,163 and U.S. Pat. No. 2,203,680) disclose the use of ammonium vanadate catalyst with nitric oxide as the oxidant. Olin et al. (U.S. Pat. No. 2,226,357) disclose the use of a catalyst such as vanadic acid, manganese, chromium, vanadium, tungsten, or compounds thereof, such as nitrates, oxides, or sulfates, in a nitric acid solution.

Drent (U.S. Pat. No. 4,868,328) discloses a process for the selective oxidative carboxylation of a conjugated diene with carbon monoxide in the presence of a catalyst to produce alkene dicarboxylic acid diester.

SUMMARY OF THE INVENTION

The present invention provides a method for making carboxylic acid from polyethylenically unsaturated compound having a pair of carbon atoms ethylenically bonded to other carbon atoms but singly bonded to each other or a pair of carbon atoms ethylenically bonded to other carbon atoms but separated from each other by a saturated carbon atom. Such a polyethylenically unsaturated compound is referred to as "PUC" herein. In the method of the present invention, a PUC is reacted with a hydroperoxide oxidant in a polar organic solvent in the presence of a catalyst which is a salt of vanadic acid for a period of time effective to oxidize the polyethylenically unsaturated compound. This method is capable of oxidatively cleaving substantially all of the polyethylenically unsaturated compound with the above polyethylenic structure, but is incapable of substantially oxidatively cleaving compounds that do not have that structure, e.g., a monoethylenically unsaturated compound, present in a mixture with a PUC. This invention is also directed to a carboxylic acid made by this method.

The present invention also provides a method for purifying a monounsaturated compound from a mixture containing the monounsaturated compound and a PUC by selectively oxidizing the PUC. In this invention, the PUC is selectively oxidized but the monounsaturated compound is not substantially affected. The unreacted material can easily be separated from the oxidation byproduct. Also, in the cleavage of the PUC, many useful products, such as carboxylic acids, can be produced.

The method of the present invention can be advantageously employed to produce certain commercially important dicarboxylic acids and monocarboxylic acids, for example, hexanoic acid and azelaic acid, by the selective oxidation of PUC. Because of the selective oxidation of the PUC, the method of the present invention can be utilized to produce a desired dicarboxylic acid or monocarboxylic acid with a reduced amount of contaminant. As previously stated, the method can also be used to purify a valuable monounsaturated compound (e.g., an ethylenically unsaturated fatty acid, oleic acid) from a mixture of a PUC (e.g., linoleic acid) and the monounsaturated compound. The preferred oxidant, hydrogen peroxide, is environmentally compatible because it disintegrates into water and oxygen. Employing this method, the risk of health hazard due to the presence of hazardous $NO_x$ gases is obviated because no strong inorganic acid is used. Further, the method of the present invention involves a relatively simple reaction which can be conducted in one reaction vessel with a single reaction step without the need for gaseous oxidants.

DETAILED DESCRIPTION OF THE INVENTION

The present invention is directed to a method that can produce carboxylic acid by selective oxidation of PUC using a relatively inexpensive and environmentally safe oxidant.

According to the present invention, at least one carboxylic acid can be made by selective, oxidative cleavage of a substrate which is a PUC. The oxidation reaction is conducted in the presence of a catalyst which is a salt of vanadic acid with a hydroperoxide oxidant in a suitable polar organic solvent.

A. SUBSTRATE

A suitable ethylenically unsaturated compound that can be selectively cleaved by the method of the present invention contains a pair of carbon atoms ethylenically bonded to other carbon atoms but singly bonded to each other or a pair of carbon atoms ethylenically bonded to other carbon atoms but separated from each other by a saturated carbon atom. In such a PUC, two carbon-carbon double bonds are separated by one or two carbon-carbon single bonds. As used herein, a moiety that contains such a pair of ethylenically (or doubly) bonded carbon atoms is referred to as a "DIENE" moiety. A compound that contains such a DIENE moiety can contain two or more carbon-carbon double bonds but does not necessarily have to be an olefin. Such an unsaturated compound is "polyethylenically unsaturated" (sometimes referred to as "polyunsaturated") because it has two or more carbon-carbon double bonds. A suitable PUC can be cleaved by the present method to produce at least one carboxylic acid.

An example of a PUC having a pair of carbon atoms ethylenically bonded to other carbon atoms but singly bonded to each other is 13-hydroperoxylinoleic acid, which has double bonds in the ninth and eleventh carbon positions. An example of a PUC having a pair of carbon atoms ethylenically bonded to other carbon atoms but separated from each other by a saturated carbon atom is linoleic acid, which has carbons on the ninth and twelfth carbon positions. Though uncommon, PUCs with more than two double bonds can also be oxidatively cleaved by the method of the present invention.

Suitable polyethylenically unsaturated compounds that can be oxidized and cleaved by the present invention include polyethylenically unsaturated olefins as well as polyethylenically unsaturated carboxylic acids and their esters. Such substance having a DIENE moiety are PUCs and can be effectively cleaved with the method of the present invention as long as it can be dissolved in one of the suitable polar organic solvents. For example, a suitable PUC cleavable with the method of the present invention is a carboxylic acid having a DIENE moiety. The preferred carboxylic acid are linear (i.e., straight chain) $C_6$ to $C_{18}$ carboxylic acids. Representative examples of suitable polyethylenically unsaturated carboxylic acids are linoleic acid, linolenic acid, arachidonic acid, 13-hydroperoxylinoleic acid, conjugated linoleic acid, alpha-elaeostearic acid, calendulic acid, alpha-parinaric acid, dimorphecoric acid, stillingic acid, and crepenic acid. Particularly preferred are naturally occurring fatty acids. The preferred fatty acids for a method of the present invention are polyethylenically unsaturated, linear $C_{10}$ to $C_{18}$ fatty acids with two carbon-carbon double bonds separated by one saturated carbon atom. Examples of such preferred fatty acids include linoleic acid and linolenic acid.

When such a polyethylenically unsaturated fatty acid is cleaved by oxidation using the method of the present invention, typically a dicarboxylic acid and a monocarboxylic acid are produced. For example, when linoleic acid is cleaved, the products are azelaic acid (a dicarboxylic acid) and hexanoic acid (a monocarboxylic acid).

Typically, fatty acids suitable for producing dicarboxylic acid and monocarboxylic acid using a method of the present invention can be obtained by hydrolyzing vegetable oils or animal oils, which are largely esters of carboxylic acids. Suitable vegetable oils include, for example, soybean oil, safflower oil, sesame oil, corn oil, olive oil, peanut oil, poppyseed oil, linseed oil, and the like. Suitable animal oils include, for example, lard, tallow, fish oil, beef tallow, and the like.

Ester of a carboxylic acid that contains a DIENE moiety can be cleaved with the present method. When an ester that contains a DIENE moiety is oxidatively cleaved, typically, a monocarboxylic acid and a monoester of a dicarboxylic acid are produced. For example, ethyl linoleate is cleaved to produce hexanoic acid and monoethyl azelaic acid. When a triglyceride containing a DIENE moiety is oxidatively cleaved, typically a monocarboxylic acid is produced, along with an ester remaining as part of the cleaved triglyceride. Hydrolysis of this ester by alkali or acid results in one or more dicarboxylic acids. Examples of esters that can be so oxidized are glycerides that contain the DIENE moiety and their corresponding DIENE-moiety-containing esters when the glycerides are transesterified with alcohol: e.g., alkyl esters such as methyl esters and ethyl esters containing the DIENE moiety. The preferred esters are esters of a DIENE-moiety-containing carboxylic acid with a primary alcohol. More preferred are such esters wherein the alcohol has 1 to 6 carbon atoms. Representative examples of preferred esters are methyl linoleate, ethyl linoleate, methyl linolenate, and ethyl linolenate.

Cyclic polyethylenically unsaturated olefins containing a DIENE moiety can also be cleaved to produce dicarboxylic acids using the method of the present invention. When the ring of an cyclic olefin opens, the double bonds are oxidized to produce carboxyl groups. For example, the cleavage of 1,3 cyclooctadiene by the method of the present invention produces adipic acid. Representative examples of suitable cyclic olefins are cyclooctadiene, cyclohexadiene, cyclooctatriene, and 1,3-cycloheptadiene. The preferred cyclic olefins have $C_6$ to $C_8$ rings.

Likewise, acyclic aliphatic olefins having a DIENE moiety can also be oxidatively cleaved with the present method. However, in acyclic aliphatic olefins such as 1,4-hexadiene, wherein the end groups are not carboxyl groups, the carboxylic acid produced in the oxidative reaction typically is a monocarboxylic acid. Suitable acyclic aliphatic olefins include, for example, butadiene, 1,4-hexadiene, 2,4-hexadiene, 1,4-pentadiene, and 1,2,4-hexatriene. For aliphatic olefins, the preferred compounds are PUCs that are straight chain dienes with external double bond. More preferred are PUCs that are straight chain $C_6$ to $C_8$ dienes with external ethylenically bonded carbon atom. An external ethylenically bonded carbon is an ethylenically bonded carbon that is also an end carbon of the compound, e.g., in the C1 position.

According to the present invention, in a typical oxidation reaction product, if adequate time is allowed for the reaction, no PUC is detected with GC/GC-MS analytical method, indicating that essentially all of the PUC has been cleaved. As used herein, the PUC is considered to be "substantially oxidized" if less than 25% of the starting unsaturated compound is detected in the finished product. In the oxidation of a polyethylenically unsaturated molecule, it is not necessary that all of the double bonds are cleaved to produce acid groups by the present invention. Although in the cleavage of a polyethylenically unsaturated carboxylic acid the dicarboxylic acid and the monocarboxylic acid are generally produced equal-molarly, other oxidization by-products may also be present. For example, in the oxidative cleavage of linolenic acid, propionic acid and azelaic acid, water and carbon dioxide can also be produced.

The catalyst system of the present invention selectively oxidizes PUC. On the other hand, monoethylenically unsaturated (commonly referred to as "monounsaturated") compounds, such as oleic acid, are not oxidized or oxidized only to a limited extent (i.e. minimally oxidized). When similar conditions are used for oxidizing PUC and for oxidizing monounsaturated compounds, typically substantially all of the PUC is oxidized whereas substantially none of the monounsaturated is oxidized. In a typical reaction wherein the starting material is a mixture of PUC and a monoethylenically unsaturated compound, the finished product contains more than 90% of the starting monoethylenically unsaturated compound. However, depending on the reaction condition and the reaction time, occasionally the finished product contains less than 90%, even as little as about 75%, of the monoethylenically unsaturated starting material. As used herein, an unsaturated material is considered to be substantially unoxidized if more than 75% of this starting unsaturated material is detected in the product of the oxidizing reaction period. Examples of monoethylenically unsaturated compounds are oleic acid, erucic acid, 2-octenoic acid, 3-hexanoic acid, and elaidic acid.

Depending on the starting material used in the oxidation reaction, the resulting dicarboxylic acid and/or monocarboxylic acids can vary. For example, when the starting material is linoleic acid, the dicarboxylic acid in the product of the oxidation reaction is azelaic acid and the monocarboxylic acid is hexanoic acid. When the starting material is linolenic acid, the resulting dicarboxylic acid in the product is azelaic acid and the monocarboxylic acid is propionic acid. In the oxidative cleavage of a polyethylenically unsaturated carboxylic acid in a mixture that also contains a monounsaturated fatty acid, the product of the oxidation reaction can also contain unoxidized starting materials as well as oxidation products of the minimally oxidized monounsaturated fatty acid. For example, in the oxidation reaction of linoleic acid in a mixture with oleic acid, the oxidation reaction product can contain hexanoic and azelaic acid as well as the unoxidized oleic acid and a small amount of pelargonic acid.

B. OXIDANT

The PUCs are oxidized by reacting with a suitable hydroperoxide oxidant in the presence of a salt of vanadic acid catalyst. In the present invention, inorganic acids such as nitric acid or sulfuric acid are not needed as oxidants. Oxidants appropriate for oxidizing the PUC are hydroperoxides. Representative examples are hydrogen peroxide, cumene hydroperoxide, t-butyl hydroperoxide, and the like. Because of its relative low cost and its capability to disintegrate into water and oxygen, hydrogen peroxide is preferred. Preferably, hydroperoxide oxidant is used in an amount of about 4 molar equivalents of peroxide to 1 double-bond equivalent. Therefore, for every double bond that is expected to be cleaved, four molecules of hydroperoxide oxidant is preferably used. For example, about 8 moles of hydrogen peroxide can be used for oxidizing one mole of linoleic acid. The excess hydroperoxide oxidant can be reduced with a reductant, such as sodium bisulfite, after the oxidation reaction.

C. CATALYST

Catalysts that are suitable for catalyzing the oxidation reaction of the present invention are salts of vanadic acid, preferably ammonium salts and alkali metal salts of vanadic acid. Although acids such as vanadic acid, sulfuric acid, hydrochloric acid, and nitric acid may be added to the reacting mixture for the purpose of pH adjustment, by themselves, such acids are ineffective as catalysts. Representative examples of preferred catalysts include sodium metavanadate, sodium orthovanadate, ammonium metavanadate, ammonium orthovanadate, potassium metavanadate, potassium orthovanadate, rubidium metavanadate, cesium metavanadate, cesium orthovanadate, lithium metavanadate, lithium orthovanadate and the like. The more preferred catalyst for the present invention is sodium metavanadate, sodium orthovanadate and ammonium metavanadate. The most preferred is sodium metavanadate. The catalysts can be used in a broad range of concentrations for catalyzing the oxidation reaction of the PUC. The amount of the catalyst used is dependent on factors such as the yield desired, the solvent, reaction temperature, and reaction time selected. Preferably, the ratio of the molar equivalent of catalyst to the molar equivalent of the polyethylenically unsaturated compound is about 1:10,000 to about 1:10. More preferably the ratio is about 1:1,000 to about 1:25. It is to be understood that in a continuous reaction wherein the reaction is conducted by passing reactants through a reactor having catalyst to achieve a specific residence time, the catalyst to unsaturated compound ratio can also vary depending on the residence time selected.

D. SOLVENT

The oxidation reaction is carried out in a polar organic solvent. Polar organic solvents are carbon-containing solvents in which the electric charges are permanently separated. Preferably, the solvent is suitable for dissolving the catalyst, the unsaturated starting material, and the oxidation reaction products. The solvent is used for providing a medium for the oxidation reaction to take place. A solvent is also useful to provide a constant temperature for the reaction to proceed. Generally the oxidation reaction is conducted at the reflux temperature of the appropriate solvent at atmospheric pressure. Generally atmospheric pressure at sea level is about 760 mm Hg or 15 Psia. Suitable solvents are polar organic compounds that are inert to (i.e. not involved in) the oxidation reaction. Representative examples of suitable solvents are alcohols such as 1-butanol, 1-octanol, tertiary butanol, tertiary amyl alcohol, and propanol, as well as ethereal solvents such as dioxane. An ethereal compound is a compound that contains the oxygen-carbon bonds that are present in diethyl ether. The preferred solvents are monohydric saturated alcohols such as 1-butanol, 1-octanol, and tertiary butanol. The more preferred solvents are 1-butanol and tertiary butanol. The most preferred solvent is tertiary butanol.

Generally, a suitable solvent is used in an amount effective for substantially dissolving the reacting starting materials and for keeping the oxidation reaction products in solution. Preferably, the oxidation reaction is carried out at a concentration of unsaturated compounds (including polyethylenically unsaturated and monoethylenically unsaturated compounds) of about 0.1 wt-% to 30 wt-%, and more preferably, about 4 wt-% to about 20 wt-% in the reacting mixture, of which the solvent is the major component.

E. CONDITIONS FOR THE OXIDATION REACTION

The oxidation reaction can be carried out at a temperature for a period of time effective to oxidize the PUCs to the corresponding dicarboxylic acids and/or monocarboxylic acids. At the end of the reaction period, substantially all of the starting PUC will have been oxidized. As previously mentioned, if adequate time is allowed for the reaction, essentially all of the PUC can be cleaved into the corresponding dicarboxylic acid and/or monocarboxylic acid. In a typical reaction, at least 75% of starting PUC is cleaved.

The oxidation reaction preferably can be carried out at atmospheric pressure at a temperature of about 40° C. to 120° C., more preferably at about 80° C. to 85° C. Typically, the reaction can be carried out by refluxing at about the atmospheric boiling temperature of the solvent selected. The selection of the reaction temperature depends on many factors, one of which is the length of time required for oxidizing substantially all of the starting PUC. At low temperatures the reaction proceeds slowly. For example, at 40° C., the oxidation of linoleic acid in tertiary butanol is typically 70% complete after 40 hours. However, at about 80°-82° C. the oxidation reaction is typically almost 100% complete in about 5 to 24 hours. Another factor in the selection of the reaction temperature is the efficiency of the catalyst. The utilization of an elevated reaction temperature results in a decrease in the efficiency of the catalyst. Adding a oxidant-catalyst mixture to an already-refluxing mixture of substrate and medium also results in reduced catalytic efficiency. The reaction temperature can also be manipulated by varying the pressure under which the reaction is conducted.

In the preferred embodiments, the oxidation cleavage reactions were generally carried out by adding the reactants, catalyst and solvent together without making special efforts to adjust the pH of the mixture. When all the ingredients of an oxidative cleavage reaction are added and mixed together, often the pH of the mixture is below about 4. The typical pH of a reaction mixture in which alcohol, such as tertiary butanol, is used as a solvent is about 0 to about 5.

The oxidative reaction can take place at a wide range of pH. In the preferred embodiments, the pH of the reaction mixture changed as the oxidative reaction progressed because no buffer was used to maintain the pH. Preferably, a moderately acidic condition is used to promote the successful cleavage of PUCs. The preferred pH is about 2 to about 5, more preferably about 3 to about 4. For example, if sodium orthovanadate is used to catalyze the oxidative cleavage of linoleic acid, and the pH of the mixture is about 6 to 7 after the ingredients are mixed together, lowering the pH of the mixture to 3 to 4 by adding concentrated HCl speeds up the oxidative cleavage reaction.

The oxidative cleavage of a polyethylenically unsaturated compound (PUC) can be accomplished by stirring, heating and maintaining a mixture of the appropriate catalyst, the PUC, and a polar organic solvent in a reaction vessel at reflux temperature of the solvent for an appropriate length of time. Generally, the longer the refluxing time, the more complete the oxidative cleavage reaction is. If sufficient time is allowed for the reaction, about 100% of the starting PUC can be cleaved. Typically, more than 70% of the starting PUC is cleaved after about 16 hours of refluxing in tertiary butanol. It is to be understood that even though the preferred embodiments described herein are batch reactions, continuous reactors can be designed and utilized for the reaction.

At the end of the reaction, when substantially all of the starting PUC has been cleaved into the corresponding carboxylic acids, excess oxidant can be removed by the addition of aqueous sodium bisulfite or by other suitable methods. Then the desired carboxylic acid in the mixture formed can be isolated. The solvent can be removed by evaporation, preferably under vacuum. The remaining material, i.e., the remainder after evaporation, can then be extracted with a suitable organic solvent. Examples of suitable organic solvents include diethyl ether, ethyl acetate, dichloromethane, and methyl acetate.

To recover the carboxylic acids, the organic extract can be evaporated to remove the extraction solvent. The resulting material can then be extracted with hot water to separate out the dicarboxylic acids. The dicarboxylic acids can be purified by subsequent recrystalization from the aqueous solution. The monocarboxylic acids will remain in the organic layer of the hot water extraction step. Conventional methods can be employed to further purify the monocarboxylic acids.

The above description is given as a typical example for purifying the carboxylic acids after the oxidation reaction. It should be understood that methods for purifying carboxylic acids are known in the art, and other equivalent methods can be employed to purify the carboxylic acids formed by the oxidation reaction.

Estimation of the extent of oxidative cleavage of the starting material can be done by gas chromatography (GC) and gas chromatography-mass spectrometry (GC-MS). Such systems are well known, routinely used in laboratories, and are commercially available. After the oxidation reaction, evaporation of the solvent, and extraction using an appropriate solvent, a sample of the extract can be analyzed to determine the percent cleavage of the starting polyethylenically unsaturated compound. The sample is first treated with diazomethane for methyl esterification and then the esterified sample is analyzed by using the appropriate analytical equipment (GC and GC-MS).

F. USE OF THE PRESENT INVENTION

The method of the present invention is well suited for the production of certain dicarboxylic acids and/or monocarboxylic acids by the selective oxidation of PUC. For example, azelaic acid and hexanoic acid can be produced by the selective oxidation of linoleic acid. Azelaic acid and hexanoic acid have many commercial applications—as ingredients for making plasticizers, lubricants, dielectric fluids, flavoring agents, synthetic fabrics, and the like. These useful carboxylic acids can be produced by oxidation of fatty acids derived from oils of vegetable or animal sources. Such sources of oil generally contain a variety of fatty acids, some of which are polyethylenically unsaturated and some of which are monounsaturated.

In the oxidative cleavage of unsaturated compounds using the present invention, monounsaturated compounds are not oxidized or are only minimally oxidized such that substantially none of the monounsaturated compound is cleaved. The method of the present invention can be used to obtain a purified monounsaturated compound (e.g., oleic acid) from a mixture of the monounsaturated compound and a PUC by first oxidizing the PUC and then isolating the monounsaturated compound from the resulting mixture after the oxidation reaction. Because of the selective oxidation of the PUCs, the method of the present invention can also be utilized to produce a desired dicarboxylic acid or monocarboxylic acid with a reduced amount of contaminant. For example, the present method can be used to make azelaic acid and hexanoic acid from a mixture of linoleic acid and oleic acid with a minimal amount of pelargonic acid in the reaction product. Also, because a high percentage of the linoleic acid is converted by the oxidation reaction whereas only a very small amount of the oleic acid is converted, the present method can be used for producing a purified stream of oleic acid.

In contrast, when conventional methods are used to cleave the fatty acids by oxidation reaction, often both the polyethylenically unsaturated and monounsaturated fatty acids are cleaved. This results in a reaction product that contains a variety of dicarboxylic and monocarboxylic acids. If the goal is to produce a specific dicarboxylic acid, such a reaction product is less desireable than a product made without oxidizing the monounsaturated carboxylic acid.

Another characteristic of the method of the present invention is that relatively environmentally compatible agents are used. The preferred oxidant is hydrogen peroxide, which disintegrates into water and oxygen. This is not true of strong inorganic acids, such as sulfuric acid or nitric acid, which are used in some conventional methods. Thus, the risk of health hazard due to the presence of hazardous chemicals such as $NO_x$ gases caused by the use of strong inorganic acid is also obviated. Further, the method of the present invention involves a relatively simple reaction which can be conducted in one reaction vessel with a single reaction step. There is also no need for gaseous oxidants.

To illustrate the practice of the present invention, the following examples are presented. But the scope of the invention should not be unduly limited thereto.

EXAMPLE 1

Cleavage of Linoleic Acid Using Sodium Metavanadate

To a well-stirred mixture of sodium metavanadate (12.1 mg, 0.1 mmol), 30% w/v hydrogen peroxide (9.0 ml) and tertiary butanol (30 ml) in a round-bottom flask with a magnetic stirrer was added linoleic acid (2.835 g, 10.1 mmol). The resulting mixture was heated to reflux (82° C.). Refluxing was maintained for 16 hours. The resulting material was then heated in a water bath of 75° C. under vacuum on a rotary evaporator to remove the tertiary butanol. After evaporation, 20 ml of 10% w/v aqueous sodium bisulfite was added and mixed with the remainder after ether evaporation. The resulting mixture was extracted with diethyl ether (15 ml) three times. The ether extracts were combined and dried with anhydrous magnesium sulfate. The dried ether extract was heated in a water bath of 75° C. under vacuum on a rotary evaporator to evaporate the ether. After evaporation, an orange oil (2.45 g) was obtained. This orange oil was dissolved in ether, and a sample of the resulting solution was taken for methyl esterification with diazomethane. The esterified sample was analyzed by gas chromatography (GC) (Varian, Sunnyvale, Calif.) and gas chromatography-mass spectrometry (GC-MS) (Hewlett Packard) using a DB-1 methyl silicone capillary column (Varian). The yield was determined by GC/GC-MS Normalization (normalization is a way of standardizing the analysis). A mixture of standards of compounds was run on the GC/GC-MS to establish the response factors for a variety of compounds, which were used to calculate the fraction percentages and the amount of the compounds in a sample of the oxidation reaction product after the sample had been run on the GC/GC-MS. The yield was calculated as a ratio between the amount present in the sample and the amount that should be present theoretically. The analytical results showed that the oil was a mixture of hexanoic acid (about 62% yield) and azelaic acid (about 59% yield). No linoleic acid was detected in the oil, indicating that essentially all of the linoleic acid was cleaved in the oxidation reaction.

EXAMPLE 2

Cleavage of Linoleic Acid Using Ammonium Metavanadate

To a solution of ammonium metavanadate (5.84 mg, 0.05 mmol), 30% w/v hydrogen peroxide (5 ml), and tertiary butanol (20 ml) in a round-bottom flask with a magnetic stirrer was added linoleic acid (1.426 g, 5 mmol). The mixture was stirred and heated to reflux temperature (82° C.). Refluxing was maintained for about 12 hours. Then the mixture was heated in a water bath of 75° C. under vacuum on a rotary evaporator to remove the tertiary butanol. The remaining material after evaporation was processed in a manner analogous to that in Example 1. The analytical results showed that the resulting oil product was a mixture (1.232 g) of hexanoic acid (about 57% yield) and azelaic acid (about 55% yield). No linoleic acid was detected in the oil, indicating that essentially all of the linoleic acid was cleaved in the oxidation reaction.

EXAMPLE 3

Cleavage of Linoleic Acid Using Less Sodium Metavanadate

Linoleic acid (2.843 g, 10 mmol) was treated with sodium metavanadate (2.45 mg, 0.02 mmol) and 30% w/v hydrogen peroxide (9 ml) in tertiary butanol (30 ml) and further processed in a manner analogous to that in Example 1. The resulting oil (2.37 g,) was analyzed using GC and GC-MS. The analytical results show that the oil was a mixture of hexanoic acid (63% yield) and azelaic acid (63% yield). No linoleic acid was detected in the product mixture.

EXAMPLE 4

Cleavage of Linoleic Acid Using Sodium Metavanadate, 5 Hours of Reflux

Linoleic acid (281.3 mg, 1.00 mmol) was treated with sodium metavanadate (12.1 mg, 0.1 mmol) and 30% w/v hydrogen peroxide (3.0 ml) in tertiary butanol (15 ml) and further processed in a manner analogous to that in Example 1, except that refluxing was maintained for five hours only. GC and GC-MS analyses of the resulting oil show that the oil was a mixture (235 mg) of hexanoic acid (about 50% yield) and azelaic acid (about 48% yield). No linoleic acid was detected in the oil.

EXAMPLE 5

Cleavage of 13-Hydroperoxylinoleic Acid Using Sodium Metavanadate

A measured amount of 13-Hydroperoxylinoleic acid (235 mg, 0.752 mmol) was treated with sodium metavanadate (4.6 mg, 0.037 mmol) and 30% w/v hydrogen peroxide (3.0 ml) in tertiary butanol (20 ml) and further processed in a manner analogous to that in Example 1. Refluxing was maintained for 15 hours. The resulting oil was esterified and analyzed by GC and GC-MS. The oil (235 mg) was a mixture of hexanoic acid (54% yield) and azelaic acid (about 53% yield). No 13-hydroperoxylinoleic acid was detected in the oil. This indicated that essentially all of the 13-hydroperoxylinoleic acid was cleaved in the oxidation reaction.

EXAMPLE 6

Cleavage of Linoleic Acid Using Sodium Metavanadate in Dioxane

To a well-stirred mixture of sodium metavanadate (26.15 mg, 0.21 mmol), 30% w/v hydrogen peroxide (3 ml), and dioxane (20 ml) in a round-bottom flask with a magnetic stirrer was added linoleic acid (561.12 mg, 2.00 mmol). The mixture was heated to reflux temperature (90° C.). Refluxing was maintained for 18 hours. The resulting material was heated in a water bath of 95° C. under vacuum on a rotary evaporator to remove the dioxane. Then 10 ml of aqueous sodium bisulfite (10% w/v) was added to the remainder after evaporation and mixed. The mixture was further processed in a manner analogous to that in Example 1. An oil was produced. The resulting oil was passed through a flash column (Kieselgel 60G, 5 g) to remove extraneous matters. Subsequently, the column was first eluted with hexane and then with ether. The hexane and ether fractions were combined. The eluent was evaporated from the eluate, resulting in an oil (459 mg). A sample of the oil was methyl esterified with diazomethane and analyzed using GC and GC-MS. The analytical results showed that the linoleic acid was cleaved into hexanoic acid and azelaic acid. The oil contained some linoleic acid. About 72% of the starting linoleic acid had been cleaved in the oxidation reaction.

EXAMPLE 7

Cleavage of Linoleic Acid Using Sodium Metavanadate in 1-Propanol

To a well-stirred mixture of sodium metavanadate (24.48 mg, 0.2 mmol), 30% w/v hydrogen peroxide (3 ml), and 1-propanol (15 ml) in a round-bottom flask with a magnetic stirrer was added linoleic acid (563 mg, 2 mmol). The mixture was heated and maintained at reflux (85° C.) for 12 hours. After refluxing, the mixture was heated in a water bath of 90° C. under vacuum on a rotary evaporator to remove the 1-propanol. The remainder after evaporation was treated with 10% w/v aqueous sodium bisulfite and further processed in a matter analogous to that in Example 1. The resulting oil was esterified and analyzed by GC and GC-MS. A mixture (about 76% yield) of hexanoic acid and azelaic acid was found in the oil. The presence of unreacted linoleic acid in the oil indicating that about 76% of the starting linoleic acid had been cleaved.

EXAMPLE 8

Cleavage of Linolenic Acid Using Sodium Metavanadate in Tertiary Butanol

To a well-stirred mixture of sodium metavanadate (6.55 mg, 0.053 mmol), 30% w/v hydrogen peroxide (7 ml), and tertiary butanol (25 ml) in a round-bottom flask with a magnetic stirrer was added linolenic acid (280 mg, 1.006 mmol). The mixture was heated and maintained at reflux (82° C.) for 24 hours. After refluxing, the mixture was heated in a water bath of 75° C. on a rotary evaporator to remove the tertiary butanol. The remainder after evaporation was treated with 10% w/v aqueous sodium bisulfite and further processed in a manner analogous to that in Example 1. The resulting oil (231 mg, about 87% total yield) was esterified with diazomethane and analyzed with GC and GC-MS. Propionic acid and azelaic acid were found in the oil. No linolenic acid was detected in the oil.

EXAMPLE 9

Treating Linoleic and Oleic Acid with Sodium Metavanadate in Tertiary Butanol To a stirred solution of sodium metavanadate (6.2 mg, 0.05 mmol), 30% w/v hydrogen peroxide (6 ml), and tertiary butanol (30 ml) in a round-bottom flask with a magnetic stirrer was added a mixture of linoleic acid (1.412 g, 5.00 mmol) and oleic acid (1.43 g, 5.00 mmol). The mixture was heated and maintained at reflux (82° C.) for 24 hours. After refluxing, the mixture was heated in a water bath of 75° C. on a rotary evaporator to remove the tertiary butanol. After evaporation, the remainder was further processed in a manner analogous to that in Example 1. An oil (2.67 g) was obtained. The oil was dissolved in ether. A sample of the resulting solution was taken for methyl esterification with diazomethane. The esterified product was analyzed by GC and GC-MS in a manner analogous to that in Example 1. The analytical results showed that essentially all of the linoleic acid had been cleaved. Hexanoic acid and azelaic acid were found in the product. Oleic acid was found to have undergone no cleavage reaction.

EXAMPLE 10

Treating Linoleic Acid and Oleic Acid with Sodium Orthovanadate in Tertiary Butanol A mixture of linoleic acid (562.4 mg, 2 mmol) and oleic acid (565.7 mg, 2 mmol) was treated with sodium orthovanadate (18.9 mg, 0.1 mmol) and 30% w/v hydrogen peroxide (6 ml) in tertiary butanol (20 ml) in a manner analogous to that in Example 9. In this example, the pH of the reaction mixture was about 6 to 7 after the addition of catalyst. The pH was adjusted to about 2 to 3 with concentrated hydrochloric acid before heating was commenced. After heating, the resulting product was further processed and analyzed in a manner analogous to that in Example 1. The analytical results showed that essentially all of the linoleic acid had been cleaved to produce hexanoic acid and azelaic acid, whereas only 6% of the oleic acid was cleaved to produce pelargonic acid and azelaic acid.

EXAMPLE 11

Treating Linoleic Acid and Oleic Acid with Ammonium Metavanadate in Tertiary Butanol A mixture of linoleic acid (561 mg, 2 mmol) and oleic acid (565 mg, 2 mmol) was treated with 30% w/v hydrogen peroxide (5 ml) and ammonium metavanadate (11.7 mg, 0.1 mmol) in tertiary butanol (20 ml) in a manner analogous to that in Example 9. The resulting material was further processed and analyzed in a manner analogous to that in Example 1. The analytical results showed that essentially all of the linoleic acid was cleaved into hexanoic acid and azelaic acid, whereas only 6% of the oleic acid was cleaved into pelargonic acid and azelaic acid.

COMPARATIVE EXAMPLE A

Treating Erucic Acid with Sodium Metavanadate in Tertiary Butanol

In 4 runs, erucic acid was treated and analyzed in a manner analogous to that for treating linoleic acid in Example 1. The following table shows the amount used and the results.

| Run no. | Amt. of Catalyst mg | Amt. of 30% Hydrogen peroxide ml | Amt. of Erucic acid mg | Cleavage % |
|---|---|---|---|---|
| 1 | 13.2 | 5 | 361 | 0 |
| 2 | 6.5 | 3 | 361 | 0 |
| 3 | 30.5 | 5 | 1696 | 0 |
| 4 | 6.1 | 3 | 1694 | 6 |

The results showed that in Runs 1 to 3, essentially all of the erucic acid remained uncleaved in the reaction. In Run No. 4, a small portion of the erucic acid was cleaved; the products were bassylic acid and pelargonic acid. Therefore, substantially all of the erucic acid was uncleaved in these runs.

COMPARATIVE EXAMPLE B

Treating Oleic Acid with Sodium Metavanadate in Tertiary Butanol

Oleic acid (282 mg, 1.00 mmol) was treated with sodium metavanadate (12.2 mg, 0.1 mmol) and 30% w/v hydrogen peroxide (3 ml) in tertiary butanol (20 ml), further processed and analyzed in a manner analogous to that for treating linoleic acid in Example 1. The results showed that the oleic acid was not cleaved.

COMPARATIVE EXAMPLE C

Treating Oleic Acid with Sodium Metavanadate in Tertiary Butanol

Oleic acid (564 mg, 2.00 mmol) was treated with sodium metavanadate (12.2 mg, 0.1 mmol) and 30% w/v hydrogen peroxide (3 ml) in tertiary butanol (20 ml), further processed and analyzed in a manner analogous to that for treating linoleic acid in Example 1. The results showed that the oleic acid was not cleaved by the treatment.

COMPARATIVE EXAMPLE D

Treating Oleic Acid with Sodium Metavanadate in Tertiary Butanol

Oleic acid was processed and analyzed in a manner analogous to that for treating linoleic acid in Example 1. The following table shows a summary of the results.

| Run no. | Amt. of Catalyst mg | Amt. of 30% Hydrogen peroxide ml | Amt. of Oleic acid mg | Cleavage % |
|---|---|---|---|---|
| 1 | 6.2 | 3 | 283 | 7 |
| 2 | 13.2 | 5 | 286 | 18 |
| 3 | 12.9 | 5 | 286 | 10 |
| 4 | 26.4 | 5 | 285 | 5 |
| 5 | 6.1 | 3 | 145 | 16 |
| 6 | 6.3 | 3 | 560 | 10 |
| 7 | 12.3 | 3 | 560 | 20 |
| 8 | 27.0 | 6 | 560 | 12 |

In these runs, some oleic acid was cleaved into pelargonic acid and azelaic acid. However, a substantial fraction of the original starting material remained uncleaved.

COMPARATIVE EXAMPLE E

Treating Oleic Acid with Sodium Metavanadate in Tertiary Butanol at pH 6-7

To a well-stirred mixture of sodium metavanadate (12.1 mg, 0.1 mmol), 30% w/v hydrogen peroxide (3.00 ml) and tertiary butanol (20 ml) in a round-bottom flask with a magnetic stirrer was added oleic acid (560 mg, 2 mmol). The mixture was adjusted to about PH 6 to 7 with concentrated sodium hydroxide, and then heated and maintained at reflux (82° C.) for 24 hours. The resulting material was further processed and analyzed in a manner analogous to that for treating linoleic acid in Example 1. The analytical results showed that only 11% of the oleic acid was cleaved.

EXAMPLE 12

Purifying Oleic Acid from a Mixture of Oleic Acid and Linoleic Acid

A mixture of linoleic acid (561 mg, 2 mmol) and oleic acid (565 mg, 2 mmol) was treated with 30% w/v hydrogen peroxide (5 ml) and ammonium metavanadate (11.7 mg, 0.1 mmol) in tertiary butanol (20 ml) in a manner analogous to that in Example 9. The resulting material was further processed to obtain an orange oil and analyzed in a manner analogous to that in Example 1. The orange oil was subjected to ethyl esterification by refluxing in a 2% w/v solution (20 ml) of concentrated sulfuric acid in ethanol. After cooling, addition of ice-cold water (20 ml), and acidification of the resulting mixture, the solution was extracted with ether three times, each with 15 ml of ether (i.e., 3×15 ml). After combining the ether extracts and drying with anhydrous magnesium sulfate, the ether and ethanol were removed by evaporation on a rotary evaporator. Ethyl hexanoate (107 mg, boiling point of 45° to 48° C.) was distilled off under water pump vacuum. The residue was hydrolysed by refluxing in a solution of potassium hydroxide (10 ml, 1.0M) in ethanol. After cooling, water (15 ml) was added, and the mixture was acidified with concentrated sulfuric acid to about pH 2. Some ethanol was removed on a rotary evaporator, and the remainder extracted with ether. Upon removal of the ether from the ether extract, the oil mixture left was extracted with hot water to separate azelaic acid (193 mg). Finally, oleic acid (342 mg) was recovered by extracting the remainder with hexane (3×5 ml). The hexane fraction was separated by leaving the mixture in a freezer (−25° C.) for 12 hours, and then separating out the hexane layer. Oleic acid was obtained upon evaporating hexane on a rotary evaporator.

EXAMPLE 13

Cleavage of an Ester

Ethyl linoleate (1.801 g, 5.84 mmol) was treated with sodium metavanadate (45.1 mg, 0.37 mmol) and 30% w/v hydrogen peroxide (5 ml) in tertiary butanol (20 ml) at a pH of about 4 (adjusted by adding concentrated HCl to the mixture), further processed and analyzed in a manner analogous to that for treating linoleic acid in Example 1. The analysis showed that 70% of the starting ethyl linoleate was cleaved into hexanoic acid and monoethyl azelaic acid.

EXAMPLE 14

Cleavage of a Diene

In tertiary butanol (20 ml) was added 1,4-hexadiene (369 mg, 4.5 mmol) and 30% w/v hydrogen peroxide (4 ml) and sodium metavanadate (27.5 mg, 0.225 mmol) in a round-bottom flask at a pH of about 4 (adjusted by adding concentrated HCl to the mixture). The materials were processed and analyzed in a manner analogous to that for treating linoleic acid in Example 1. The analysis showed that 60% of the starting 1,4-hexadiene was cleaved to form acetic acid.

Various modifications and alterations of this invention will become apparent to those skilled in the art without departing from the scope and spirit of this invention.

What is claimed is:

1. A method for making carboxylic acid from a polyethylenically unsaturated compound containing a pair of carbon atoms ethylenically bonded to other carbon atoms but singly bonded to each other or a pair of carbon atoms ethylenically bonded to other carbon atoms but separated from each other by a saturated carbon atom, said method comprising reacting the unsaturated compound with a hydroperoxide oxidant in the presence of a salt of vanadic acid in a polar organic solvent.

2. The method of claim 1 wherein the unsaturated compound is a carboxylic acid, ester thereof, or olefin.

3. The method of claim 2 wherein the unsaturated compound is a linear fatty acid.

4. The method of claim 2 wherein the unsaturated compound is an ester of a fatty acid and a monohydric primary alcohol.

5. The method of claim 2 wherein the unsaturated compound is a cyclic olefin.

6. The method of claim 2 wherein the unsaturated compound is an acyclic diene with an external ethylenically bonded carbon atom.

7. The method of claim 2 wherein the unsaturated compound is a linear $C_6$ to $C_{18}$ compound.

8. The method of claim 1 wherein the unsaturated compound is selected from the group consisting of linoleic acid, linolenic acid, arachidonic acid, 13-hydroperoxylinoleic acid, conjugated linoleic acid, alpha-elaeostearic acid, calendulic acid, alphaparinaric acid, dimorphecoric acid, stillingic acid, crepenic acid, esters thereof; cyclooctadiene, cyclohexadiene, cyclooctatriene, 1,3-cycloheptadiene, butadiene, 1,4 hexadiene, 2,4-hexadiene, 1,4-pentadiene, and 1,2,4-hexatriene.

9. The method of claim 1 wherein the salt of vanadic acid is selected from the group consisting of sodium metavanadate, sodium orthovanadate, ammonium metavanadate, ammonium orthovanadate, potassium metavanadate, potassium orthovanadate, rubidium metavanadate, cesium metavanadate, cesium orthovanadate, lithium metavanadate, lithium orthovanadate, and mixtures thereof.

10. The method of claim 1 wherein the salt of vanadic acid and the ethylenically unsaturated compound are mixed at a molar ratio of about 1:10000 to about 1:10.

11. The method of claim 1 wherein the solvent is selected from the group consisting of alcohols and water-miscible ethereal solvents.

12. The method of claim 11 wherein the solvent is selected from the group consisting of tertiary butanol, 1-propanol, 1-octanol, dioxane, tertiary amyl alcohol, and mixtures thereof.

13. The method of claim 1 wherein the oxidant is selected from the group consisting of hydrogen peroxide, tertiary butyl hydroperoxide, cumene hydroperoxide, tertiary amyl hydroperoxide, and mixtures thereof.

14. The method of claim 1 wherein the reaction is conducted at a temperature of about 40° C. to about 120° C.

15. The method of claim 1 wherein:
(a) the polyethylenically unsaturated compound is selected from the group consisting of linoleic acid, linolenic acid, 13-hydroperoxylinoleic acid, conjugated linoleic acid, alpha-elaeostearic acid, calendulic acid, alpha-parinaric acid, dimorphecoric acid, stillingic acid, and crepenic acid;
(b) the solvent is tertiary butanol;
(c) the oxidant is hydrogen peroxide;
(d) the salt of vanadic acid is sodium metavanadate;
(e) the reaction is conducted at a temperature of about 82° C.; and
(f) the reaction is conducted for a period of about 5 to 24 hours.

16. A method of selectively oxidizing an polyethylenically unsaturated compound containing a pair of carbon atoms ethylenically bonded to other carbon atoms but singly bonded to each other or a pair of carbon atoms ethylenically bonded to other carbon atoms but separated from each other by a saturated carbon atom to produce carboxylic acid, said method comprising reacting a hydroperoxide oxidant with a mixture containing a monoethylenically unsaturated compound and the polyethylenically unsaturated compound in the presence of a salt of vanadic acid in a polar organic solvent, wherein substantially all of the polyethylenically unsaturated compound is oxidized and substantially all of the monoethylenically unsaturated compound is unoxidized.

17. The method of claim 16 wherein the polyethylenically unsaturated compound is a carboxylic acid, ester thereof, or olefin.

18. The method of claim 16 wherein the polyethylenically unsaturated compound is a linear $C_{10}$ to $C_{18}$ fatty acid.

19. The method of claim 16 wherein azelaic acid and hexanoic acid are produced.

20. A method of selectively oxidizing linoleic acid to produce hexanoic acid and azelaic acid, said method comprising reacting hydrogen peroxide with a mixture containing linoleic acid and oleic acid in the presence of an effective amount of sodium metavanadate in tertiary butanol for about 12 to 20 hours at about 82° C. at atmospheric pressure, wherein more than 90% of the linoleic acid is oxidized and less than 25% of the oleic acid is oxidized.

21. A carboxylic acid made by reacting a polyethylenically unsaturated compound containing a pair of carbon atoms ethylenically bonded to other carbon atoms but singly bonded to each other or a pair of carbon atoms ethylenically bonded to other carbon atoms but separated from each other by a saturated carbon atom with a hydroperoxide oxidant in the presence of a salt of vanadic acid in a polar organic solvent.

22. A method for purifying a monoethylenically unsaturated compound from a mixture containing said monoethylenically unsaturated compound and a polyethylenically unsaturated compound containing a pair of carbon atoms ethylenically bonded to other carbon atoms but singly bonded to each other or a pair of carbon atoms ethylenically bonded to other carbon atoms but separated from each other by a saturated carbon atom, said method comprising:

(a) reacting a hydroperoxide oxidant with the mixture in the presence of a salt of vanadic acid in a polar organic solvent for a period of time effective to oxidize substantially all of the polyethylenically unsaturated compound, wherein substantially all of the monoethylenically unsaturated compound is unoxidized and wherein oxidation products are produced, forming a second mixture; and (b) isolating the monoethylenically unsaturated compound from the second mixture of step (a).

* * * * *